(12) United States Patent
Leivian et al.

(10) Patent No.: US 6,580,973 B2
(45) Date of Patent: Jun. 17, 2003

(54) METHOD OF RESPONSE SYNTHESIS IN A DRIVER ASSISTANCE SYSTEM

(76) Inventors: Robert H. Leivian, 2702 W. Curry, Chandler, AZ (US) 85224; Clifford A. Wood, 7227 S. Bonarden, Tempe, AZ (US) 85283

( * ) Notice: Subject to any disclaimer, the term of this patent is extended or adjusted under 35 U.S.C. 154(b) by 0 days.

(21) Appl. No.: 09/976,560

(22) Filed: Oct. 12, 2001

(65) Prior Publication Data

US 2002/0120371 A1 Aug. 29, 2002

Related U.S. Application Data

(60) Provisional application No. 60/240,443, filed on Oct. 14, 2000, provisional application No. 60/240,444, filed on Oct. 14, 2000, provisional application No. 60/240,493, filed on Oct. 14, 2000, provisional application No. 60/240,560, filed on Oct. 16, 2000, and provisional application No. 60/240,553, filed on Oct. 14, 2000.

(51) Int. Cl.$^7$ ................................................. G05D 7/00
(52) U.S. Cl. ........................................................ 701/1
(58) Field of Search ............................... 701/1, 29, 33, 701/34

(56) References Cited

U.S. PATENT DOCUMENTS

| | | | |
|---|---|---|---|
| 5,769,085 A | 6/1998 | Kawakami et al. | |
| 5,808,374 A | 9/1998 | Miller et al. | |
| 6,249,720 B1 | * 6/2001 | Kubota et al. | ................. 701/1 |

FOREIGN PATENT DOCUMENTS

| | | |
|---|---|---|
| DE | 198 21 163 A1 | 11/1999 |
| EP | 0 293 121 A2 | 11/1988 |
| EP | 0 978 433 A2 | 2/2000 |
| JP | 01195139 | 8/1989 |
| JP | 10-313359 | 11/1998 |
| WO | WO 00/55000 | 9/2000 |
| WO | WO 00/58131 | 10/2000 |

OTHER PUBLICATIONS

Remboski et al., "Driver Performance Improvement through the Driver Advocate: A Research Initiative toward Automotive Safety", SAE Technical Paper Series, Oct. 16–18, 1999, 12 pgs., SAE International.

English Translation of the International Search Report for Application No. PCT/US01/32103, filed Oct. 15, 2001.

* cited by examiner

*Primary Examiner*—Yonel Beaulieu
(74) *Attorney, Agent, or Firm*—Marshall, Gerstein & Borun

(57) ABSTRACT

A method (600) of synthesizing a response to an operating situation of a vehicle includes the step of generating a master condition list (602), determining the existence of an operating situation (604), determining an operator cognitive load (606) and determining a response to the operating situation based in part on the master condition list and the operator cognitive load (608). The master condition list is a fusion of sensor data gathered within and around the vehicle. The operator cognitive load is a measure of the operator's ability to handle tasks within the vehicle.

20 Claims, 3 Drawing Sheets

METHOD OF RESPONSE SYNTHESIS IN A DRIVER ASSISTANCE SYSTEM

CROSS-REFERENCE TO RELATED APPLICATIONS

The present application claims priority to U.S. Provisional Application Serial No. 60/240,443, filed Oct. 14, 2000 entitled "System for Real-Time Driving Performance Assessment;" U.S. Provisional Application Serial No. 60/240,444, filed Oct. 14, 2000 entitled "A System for Driver Assistance and Driver Performance Improvement;" U.S. Provisional Application Serial No. 60/240,493, filed Oct. 14, 2000 entitled "Driver's Cell Phone Assistant;" U.S. Provisional Application Serial No. 60/240,560, filed Oct. 16, 2000 entitled "Response Selector: A Method of Response Synthesis in Driver Assistance System;" and U.S. Provisional Application Serial No. 60/240,553, filed Oct. 14, 2000 entitled "A System for Driver Performance Improvement," the disclosures of which are hereby incorporated herein by reference.

FIELD OF THE INVENTION

The present invention relates generally to the field of vehicle operation, and more particularly, to a method and apparatus for assessing and improving the performance of a vehicle operator.

BACKGROUND OF THE INVENTION

The flood of information reaching drivers—telematics, infotainment, collision warning and others—requires a new approach to the operator-vehicle interface. At present, information (such as navigation instructions, cell phone and email messages, traffic warnings, infotainment options, vehicle condition monitoring, etc.) is presented to the vehicle operator asynchronously taking no account of how demanding the driving task might be in a given moment. For example, a "check engine" indicator light might light up among the instruments at the same time a driver is putting a CD into the stereo system, while the navigation system screen displays an upcoming turn and gives a verbal description of that turn, as a cell phone call comes into the car and the driver is engaged in conversation with one or more passengers.

Human beings have a finite ability to perceive the environment, to attend to elements of the environment, to cognitively process the stimuli taken in, to draw appropriate meaning from perceptions, and to act appropriately upon those perceived meanings. Furthermore, there is great variation within the driving population in both native and developed abilities to drive. Thus, vehicle operators are subject to confusion, distraction, and to ignorance, which is exacerbated by the barrage of stimuli they are now subjected to while operating a vehicle. Training, experience, and technology can be used to mitigate confusion, distraction, and ignorance. Unfortunately, in the United States there is little formal or informal training in the skills involved in driving, beyond the period when people first apply for their licenses. Driver training programs have not proven to be particularly effective, nor is training continued through the driving career. In fact, in the United States, in particular, most people think of driving as a right rather than a privilege. Further, studies show that most think of themselves as good drivers and of "the other person" as the one who creates problems. Unless and until a cultural or legal change takes place that encourages drivers to wish to improve their driving skill, it seems that technological solutions designed to minimize confusion, distraction, and ignorance have the best potential for improving the safety of the highway transportation system, which system is likely to become more crowded and, with little or no expansion of the roadway infrastructure likely to occur, therefore, also more dangerous in the future.

To address these and other safety concerns, an integrated safety system based on a state transition model has been proposed. The underlying concept is a "hierarchy of threat" model that steps through a series of states each one representing an assessment of the danger of an impending collision based on information from external object detectors and in-vehicle sensors. The states are "normal driving state," "warning state," "collision avoidable state," "collision unavoidable state," "post-collision state." Sensor and data fusion algorithms combine information from the sensors and determine the degree to which the danger of collision exists. If the system detects the danger of a collision it issues warnings to the driver or, in some situations, takes control of the vehicle and initiates automatic braking, automatic lane change, or other forms of vehicle control. This system represents an attempt to bring previously unrelated sensor information into an integrated state from which useful inference about the danger of collision may be made and warnings to the driver, or actual control of the vehicle, can be used to avoid completely or mitigate the damage from a collision.

There has also been proposed a system that provides extensive monitoring of the vehicle and traffic situation in order to prioritize presentation of information to the driver. The goal of this system is to manage the stream of information to the driver while taking account of the driving task, conditions, and the physical, perceptual and cognitive capacities of the driver. The support provided is designed to improve the driver's focus and to re-focus the attention of a distracted driver as s/he undertakes navigation, maneuvering and control of the vehicle. The overall system architecture incorporates an analyst/planner that accepts inputs from sensors, includes a stored repertoire of driving situations, and records information about the driver. Additionally, the system includes a dialogue controller for managing communication with the driver. The system also monitors the driver and integrates the driver's condition into the decisions made by the warning and control systems.

None of the existing systems undertake the monitoring of a range of sensor data, nor do they provide for evaluation of the driver's cognitive load. Such systems additionally fail to consider the driver's activity in the cockpit that is not directly related to the driving task such as opening and closing windows, tuning the radio, etc. For example, existing systems either do not monitor the driver at all, or monitor the driver relative to static "model" behavior as opposed to actual dynamic driver performance and/or habits. Thus, these systems do not provide information in synchronization with the driving task, nor do they attempt to minimize distractions and/or to redirect a distracted driver's attention to critical events.

Additionally, previous systems that have attempted to assess driver performance have been limited to lane-following capability, that is, evaluating how well the driver maintains the position of the vehicle relative to the edges of the lane in order to generate a parameter representing the driver's lane-following ability. The parameter is periodically determined, and if it falls below an established level, a warning, such as a buzzer or visual indication, is presented to the driver. This system is limited in that it only provides lane-following evaluation and does not account for deliberate lane departures such as to avoid a hazard, is not integrated to receive a spectrum of sensor input, and does not include driver condition and driver activity data. Though such a measure will identify degraded vehicle control, it is questionable whether it will identify cognitive or mental distraction.

Furthermore, none of these systems provide feedback to the driver relative to their overall performance, nor do they provide feedback relative to improving driver performance.

Thus, there is a need to provide information to the vehicle operator in synchronization with the driving task so as to improve operator focus, minimize distractions and ensure the operator's ability to assimilate and use the information. There is a further need to re-direct a distracted operator's attention from non-mission critical activities to prioritized information and/or tasks necessary to maintain safe operation of the vehicle. There is an additional need to provide feedback to the vehicle operator relating to performance and to provide additional feedback designed to assist the operator in improving performance.

BRIEF DESCRIPTION OF THE DRAWINGS

The invention is described in terms of several preferred embodiments with reference to the attached figures wherein like reference numerals refer to like elements throughout.

DETAILED DESCRIPTION OF THE PREFERRED EMBODIMENTS

A system is adapted to assess information incoming to a vehicle operator, to prioritize the information based upon a number of conditions relating to the vehicle operation, the operating environment, the activity of the operator and the physical condition of the operator, and to provide to the operator the most pertinent information for the given set of conditions. As used throughout this specification, the terms vehicle operator and driver are used interchangeably and each are used to refer to the person operating the vehicle in the manner in which the vehicle is intended to be operated.

In another embodiment of the invention, the system monitors various data sources, including the vehicle operation, the operating environment, the activity of the operator and the condition of the operator, and provides an assessment of the operator's performance. In doing so, the system may additionally identify the particular vehicle operator such that the assessment may be made relative to operator preferences, past driving performance and habits.

The system is further adaptable to assist the operator in improving performance. The system monitors various data sources, including the vehicle operation, the operating environment, the activity and condition of the operator, over a period of operation and records the operator's performance. The performance may be compared with accepted good practices, and a report may be provided to the operator indicating how the operator's performance compares with the accepted good practices and/or with the operator's previous driving performance and/or habitual behavior. The system may record operator performance over a number of periods of operation, and provide comparisons of operator performance from period to period.

The system is further adaptable to act in response to an assessment of the vehicle operation, the operating environment, the activity of the operator and the condition of the operator to avoid or mitigate a problem situation associated with operation of the vehicle.

Figure 1:
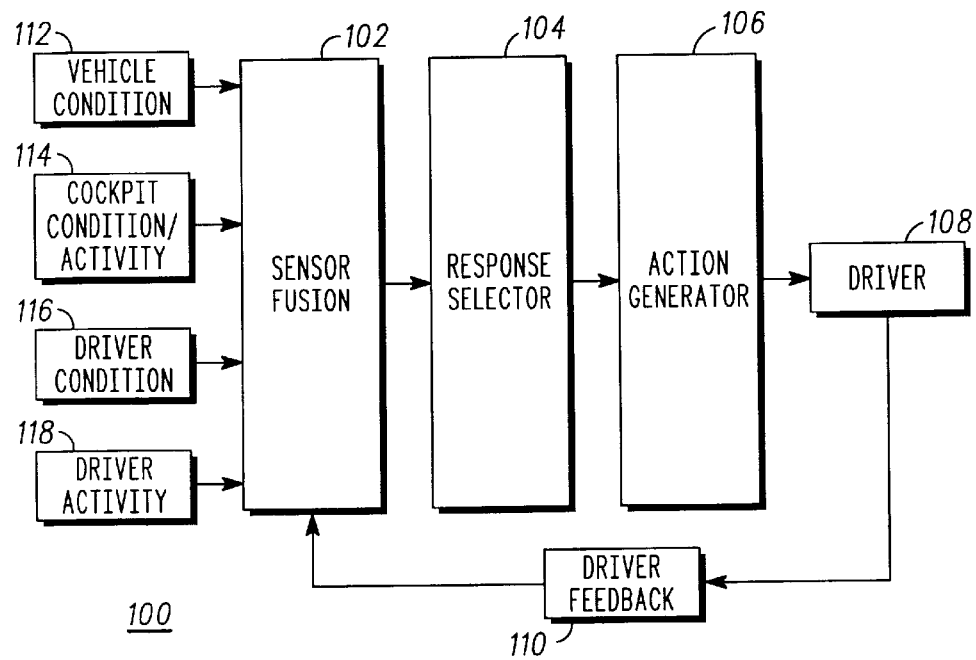
FIG. 1 is a block diagram of an operator performance assessment system in accordance with a preferred embodiment of the invention.

Referring then to FIG. 1, a system 100 includes a sensor fusion module 102, a response selector module 104 and an action generator 106. The sensor fusion module 102, response selector module 104 and action generator 106 are illustrated in FIG. 1 as separate elements for purposes of clarity and discussion. It will be appreciated these modules may be an integrated into single module. Moreover, it will be appreciated that each of these modules, or an integrated module, may include a suitable processing device, such as a microprocessor, digital signal processor, etc., one or more memory devices including suitably configured data structures, and interfaces to couple the system 100 to various vehicle sensors and to interface with a driver 108.

The sensor fusion module 102 receives data from numerous sources within and surrounding the vehicle. As illustrated in FIG. 1, the sensor fusion module 102 receives vehicle operating data 112, vehicle environment data 114, driver condition data 116 and driver activity data 118.

The vehicle operating data 112 encompasses data produced by the various vehicle sensors. Vehicle condition monitoring sensors are pervasive in an automobile. These sensors monitor numerous parameters such as engine operating parameters, vehicle speed, transmission and wheel speed, vehicle acceleration in three axes, chassis function, emission control function, etc. These sensors may also provide data related to vehicle diagnostics.

Vehicle environment data 114 encompasses data related to the environment in which the vehicle is operating, e.g., the road conditions, traffic conditions, weather, etc. The vehicle environment data 114 may be provided by sensors that also provide vehicle-operating data 112. For example, road surface and traction estimates may be provided by anti-lock braking, traction control and chassis control system sensors. Vehicle location may be provided by an on-board navigation system utilizing global positioning system (GPS) technology, or location information may be provided by a wireless communication device (e.g., a cellular telephone) and associated wireless communication network. Radar, laser, ultra-sonic and video systems can provide a map of objects near the vehicle and their motion relative to the vehicle. Weather and time of day may also be monitored directly or derived from reported sources.

Driver condition data 116 and driver activity data 118 may be provided by various cockpit monitoring systems. Seat sensors and/or infrared sensors may sense the number and locations of passengers in the vehicle. Floor and steering wheel sensors may indicate the position of the driver's feet and hands. Video or imaging sensors may monitor head, body, hand and feet movements of the driver, and the operative states and driver usage of infotainment and telematics systems may also be monitored.

As will be appreciated, numerous sources of data exist within and about the vehicle environment, which may be utilized by the system 100. Several data types have been described above, others will be described in connection with the operation of the system 100, and still others not specifically referred to herein may be used without departing from the scope and spirit of the invention. It will be appreciated that as new technologies introduce new types and sources of data and new types and sources of information into the vehicle, the system 100 may be adapted to utilize these additional sources of data to manage how the existing and new sources of information are presented to the driver.

In other words, the system 100 will monitor anything of a technical nature that the driver might be touching or using in the cockpit of the vehicle so that the system 100 knows as much as possible about what the driver is doing at any given moment. Further, the use of video or imaging technology, seat sensors and microphones in the cockpit allows the system 100 to determine the location and position of the driver, the noise level, and the presence of passengers and other potential sources of distractions. The radar, laser, video and infra-red sensors deployed around the perimeter of the vehicle monitor traffic and weather conditions, obstacles, lane markings, etc. The drivers' present condition and driving performance is inferred from direct measures, such as video, and from comparison of current performance with past performance and known good performance practices.

In addition to obtaining data from a variety of sources, the system 100 interfaces with the vehicle operator/driver 108. While operating the vehicle, the driver 108 is engaged in a number of different actions, such as, but certainly without limitation, applying the accelerator or brakes, turning the steering wheel, checking blind spots, adjusting the radio, receiving a cellular telephone call, obtaining navigation information, carrying on a conversation with a passenger, quieting the kids in the rear seat, etc. Each of the driver's actions, which for discussion purposes are illustrated as box 110 in FIG. 1, are fed back to the sensor fusion module 102 via the sensors. Additionally, as will be described in greater detail, the system 100 presents information, actions and tasks to the driver 108 via the action generator 106. This "closed" loop operation may continue for a given situation until the situation is resolved. In one very limited example to illustrate the concept, a change oil soon indication may be generated by the powertrain management system on the vehicle. Previously, this indication would cause a "service engine" or "change engine oil" light to be illuminated on the vehicle instrument panel as soon as the powertrain management system generated the indication. The light suddenly appearing among the instruments may temporarily distract the driver. If at the time the light is illuminated the driver is negotiating traffic or otherwise in a situation requiring full attention to the driving task, the distraction may present a hazard. In accordance with the preferred embodiments of the invention, the non-critical data relating to changing the engine oil may be saved until conditions allow for the information to be presented to the driver at a time less likely to create a hazard situation. In that regard, the system 100 operates continuously taking in data and re-timing its presentation to the driver. Moreover, the system 100 continuously evaluates the information to be provided to the driver to determine when and how to best provide it to the driver. This operation of the system 100 may be illustrated by an additional example. A low fuel alert may initially be a non-critical piece of information relative to current driving conditions but may become a critical piece of information if the driver is about to pass the last gas station, as system 100 is informed by the on-board navigation system, within the remaining range of the vehicle.

Figure 2:
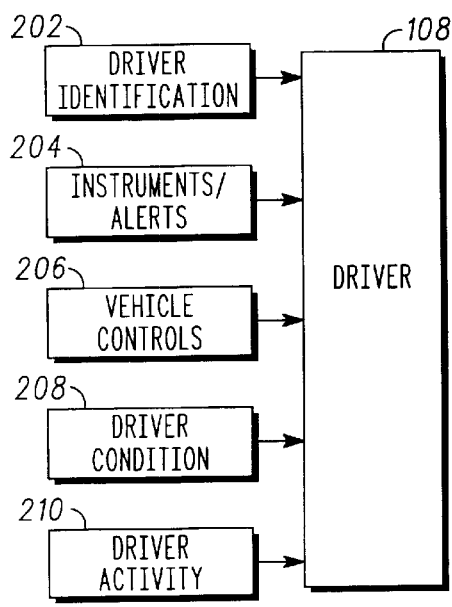
FIG. 2 is block diagram illustrating an interface of the driver with the vehicle in accordance with a preferred embodiment of the invention.

Referring to FIG. 2, a number of interfaces exists between the driver 108 and the vehicle and hence to the system 100. Various interfaces are discussed below, and may include driver identification 200, instrumentation and alerts 202, vehicle controls 204, driver condition sensors 206 and driver activity sensors 208.

Due to the wide variation in human skill-levels, physical size, and personal preferences and tastes, there are many situations where it would be useful for the system 100 to "recognize" who is attempting to enter and/or drive the vehicle. In that regard, the driver identification interface 200 may be configured as a personal portable user interface (PPUI). A PPUI may exist in many forms, but in essence captures preference, performance and habit data associated with a particular driver. The PPUI may be encoded on a smart card or embedded in the vehicle to be activated by a fingerprint reader, voice recognition system, optical recognition system or other such means.

In various embodiments, the PPUI may function as a security system granting or limiting access to the vehicle or the vehicle's ignition system, and bars access to unauthorized persons or disables the vehicle when an unauthorized person attempts to drive the vehicle. The PPUI may also capture driver preferences as it relates to a number of active safety features. Through the PPUI (driver identification interface 200), the system 100 is informed of the driver preferences. For example, the driver may select what types, under what conditions and how alerts are communicated. For example, a driver may prefer to receive an alert each time the system 100 detects too short a headway relative to a speed of travel. For another driver, a high level of alert might be perceived as a nuisance resulting in the alerts being ignored and/or the system 100 being disabled. Similarly, a driver may wish to have immediate access to all in-coming cell phone calls, while another driver may wish to have only certain calls put through. The PPUI as part of the driver identification interface 200 permits each operator of the vehicle to establish choices ahead of time.

The PPUI may also function in a driver performance improvement and/or driving restriction enforcement tool. The PPUI may be used to monitor driving performance and report to a traffic enforcement authority. This would allow a habitual traffic offender to retain driving privileges in a court-monitored fashion. Driving performance may be recorded for subsequent review, and a method of improving driver performance is described herein. Additionally, the PPUI may be used to implement controls on the usage of the vehicle. For example, a parent may restrict the distances and locations a vehicle may be taken or the hours of the day the vehicle may be operated by a newly licensed driver. An employer may monitor the driving habits of its fleet drivers.

In operation, the system 100 is programmed to recognize, based on the received data, "situations" and "conditions" that might arise during operation of a vehicle. The system 100 may be configured to actuate, relative to priorities for the presentation of information and the thresholds for the levels of alerts, warnings, and alarms. The driver identification interface 202 including the PPUI provides the driver with choices relating to the priorities, thresholds and interfaces, and operates to synchronize the choices with the appropriate driver.

The instrumentation and alerts interface 204 is used by the system 100 to inform, advise and in the appropriate situations alert and warn the driver 108. The instrumentation and alerts interface 204 may include visual, audio, haptic or other suitable indicators. Visual indicators may include gages, lighted indicators, graphic and alphanumeric displays. These visual indicators may be located centrally within the instrument panel of the vehicle, distributed about the vehicle, configured in a heads-up-display, integrated with rearview and side view mirrors, or otherwise arranged to advantageously convey the information to the driver 108. The audio indicators may be buzzers or alarms, voice or other audible alerts. The haptic alerts may include using the chassis control system to provide simulated rumble stripes, pedal or steering wheel feedback pressure, seat movements and the like. The actuation of any one or more of the indicators or alerts is controlled by the system 100 in order to synchronize the timing of information as it is provided to the driver.

The vehicle controls interface 206 includes the primary controls used by the driver to operate the vehicle. These controls include the steering wheel, accelerator pedal, brake pedal, clutch (if equipped), gear selector, etc. These controls may include suitable position and/or actuation sensors and may further include at least in the case of the accelerator pedal, brake pedal and steering wheel rate of input and/or force of input sensors. Additional sensor data may include yaw rate of the vehicle, wheel speed indicating vehicle speed and traction, tire pressure, windshield wiper activation and speed, front and/or rear window defogger activation, audio system volume control, and seat belt usage sensors.

The driver condition interface 208 utilizes various sensors to infer driver condition. For example, an alert driver continuously makes steering corrections to maintain the vehicle in its lane. By monitoring steering wheel sensors, the system 100 gathers data about the frequency and amplitude of the corrections to infer if the driver has become impaired. Speed sensors may also be queried in a similar manner. Video or other imaging sensors provide direct measurement of the drivers' condition via monitoring of such criteria as driver blink rate and gaze.

The driver activity interface 210 utilizes various sensors and imaging technology to determine the activity of the driver. That is, to determine if the driver, in addition to operating the vehicle, is adjusting the radio or heating, ventilation and air conditioning (HVAC) controls, initiating or receiving a wireless communication, receiving navigation information, and the like. These sensors may include seat pressure sensors to determine the number of passengers in the vehicle, and the activities of the passengers and video or other imaging technology to observe the driver's movements.

Referring again to FIG. 1, and as previously noted, the sensor fusion module 102 receives all of the various sensor inputs, including those measuring vehicle condition, driver condition, driver activity and operating environment (e.g., weather, road and traffic conditions), and produces a set of conditions or master condition list. The conditions represent the current discrete state of each thing the sensor fusion module 102 is monitoring. For example, the speed condition may be in one of the following states at any point in time: "stopped," "slow," "normal," "fast," and "speeding." The states are determined based upon learned thresholds between the states and based on history and known good practices. The sensor fusion module 102, given the master condition list, evaluates the current drivers tasks and activities, such as tuning the radio, listening to e-mail or other potentially distracting tasks, to produce an estimated driver cognitive load. The cognitive load of each static task may be determined externally by controlled experiments with a set of test subjects (e.g., tuning the radio might use 15.4 percent of a driver's attention). The total cognitive load is the weighted sum of each of the individual tasks. The weighting may be fixed or may change, for example exponentially, given the number of concurrent tasks.

The master condition list and the estimated driver cognitive load is then provided to the response selector module 104. The response selector module looks at the conditions, current driving situation and cognitive load to determine if a problem exists and further assesses the severity of the problem. The response selector module 104 further takes into account driver preferences, to choose a response appropriate to the driver's present task and prioritizes the presentation of alerts, warnings and other information to the driver. The response selector module 104 may incorporate a reflex agent that uses decision tree or look-up tables to match states with desired actions. Alternatively, an adaptive, i.e., learning, goal-seeking agent may be used. Thus, the response selector module 104 synthesizes and summarizes sensor data creating a correct response to any given condition change.

In one possible implementation, the response selector module 104 may include programmer-entered parameters which are used to determine if a condition change a) creates a problem, b) solves a problem, c) escalates a problem, d) initiates a driver task, e) initiates an agent task, f) completes a driver or agent task, g) changes the situation or h) is innocuous. The estimated cognitive load may be used to determine an urgency of an identified problem or whether a response to the problem should be initiated by the driver or by an agent. For example, an incoming cellular phone call may be directed to the driver if the driver's estimated cognitive load is below a threshold value for receiving cellular telephone calls. If the driver's cognitive load exceeds the threshold value for receiving cellular telephone calls, then the cellular telephone call may be forwarded to voice mail (i.e., an agent device).

The response selector 104 activates the action generator 106 in order to effect the selected response. The action generator 106 may be a library of actions that the system is equipped to perform, such as in the above example, forwarding a cellular telephone call to voice mail. The library may include actions along with instructions, which may be software instructions for causing the associated processor to act, i.e., to actuate all potential alerts and warnings that can potentially be provided to the driver.

Fusion of sensor data, including data relating to the driver's condition and activity allows the system 100 to operate to assess driver performance. As noted, the system 100 is operable to identify a driver through the driver identification interface 200. During operation of the vehicle by the driver, the system 100 monitors several aspects of driver performance to arrive at a driver performance assessment value.

In one embodiment, the system 100 may monitor the driver's lane following ability. Information on laneexceedence is recorded relative to the use of turn signals and to subsequent movement of the vehicle to determine whether the lane change was intentional or unintentional. Additionally, the system 100 may monitor gaze direction, blink rates, glance frequency and duration to determine the driver's visual scanning behavior including the use of mirrors and "head checks" when changing lanes. The information may be used in comparison to known "good habits" to assess performance, and at the same time, may be used to develop a metric reflecting the driver's normal patterns, which can be used as a baseline to compare changes in driving behavior as well as to monitor degradation or improvement in driving skill.

Additional information that may be taken into consideration to assess driver performance includes application of the accelerator and brakes. The driver's use of the accelerator and brakes is recorded and given a numeric value. Again, using comparison algorithms to known "good habits" and to past performance an assessment of how smoothly the driver is braking and/or accelerating may be made as well as the number and severity of panic stops. Accelerator and brake pedal data may also be used in conjunction with metrics of headway maintenance, as monitored by the system 100. Doing so allows the system 100 to determine whether the driver is waiting too long to brake relative to obstacles in the forward path of the vehicle and even to determine whether the driver is prone to unsafe headway when vehicle speed control devices are used.

In addition to assessing driver performance, the system 100 may be adapted to assist in the improvement of driver performance. Communication of the driver assessment to the driver encourages the driver to perform better. The system 100 may also provide specific advice relating to improving driver performance. For example, the monitoring of driver performance may extend temporally (recording and comparing the driver's performance over time) and spatially (considering performance variation on familiar, frequently-traveled routes) to include all of the times that a particular driver has driven the equipped vehicle. The driver assessment, i.e., driver performance, including alerts, warnings and suggestions for improved performance, is then provided to the instrumentation/alerts module 202 for communication to the driver. A library of pre-recorded messages to the driver may be accessed by the system 100 and appropriate messages constituting reports and suggestions, are chosen. For example, the system 100 may have detected that the driver has not been doing head-checks before changing lanes, and may draw the driver's attention to that fact and state the reason that merely glancing at the mirror is not a good substitute for a head-check. Additional messages may include reminders about improving fuel economy or specifically identify an area of driving performance that deteriorated over the course of trip.

Communication of performance improvement information may be made real time; however, to avoid creating further distractions for the driver, the information may be stored and communicated to the driver following a driving activity. Triggering events and/or thresholds may be used to actuate delivery of the performance improvement messages. Alternatively, the driver may optionally select to activate the interface. The stored performance information may also be downloaded from the vehicle and used as part of a classroom or simulator-based continuing training program, a driver skills assessment program or a traffic enforcement program.

To encourage usage of the system 100 to improve driving performance, the feedback may be configured to appeal to particular categories of drivers. For example, for younger drivers, voice and likenesses of motor racing personalities may be used to convey the information, while for other drivers well known and trusted personalities may be used.

One particularly example of potential driver distraction relates to usage of cellular telephones. As described, the system 100 synthesizes and prioritizes all incoming information, including cellular telephone calls. For example, the system 100 may provide two potential cut-offs of cellular telephone calls to a driver without completely prohibiting calls. In the first instance, the caller is informed, by a pre-recorded message, that the call is being completed to a person presently driving a vehicle. The caller is then given the option of having the call sent directly to voice mail or putting the call through to the driver. Before the call is completed to the driver, the system 100 evaluates the situation, conditions and the driver's cognitive load to determine if the response, sending the call through, is appropriate. If the system 100 determines that the potential for driver distraction is beyond certain desired limits, e.g., the required driver cognitive load will exceed a threshold, the incoming call may be held and/or automatically transferred to voice mail with an appropriate pre-recorded message.

The system 100 may be configured to substantially limit the number of calls coming in to the driver. Many times a caller does not know the person they are calling is driving, and if they did, may not have called. As described above, the system 100 provides a mechanism for informing the caller that they are calling a driver and provides the option to divert the call to voice mail. Alternatively, the system 100 may be configured to give the driver the option of accepting calls transparent to the caller. In such an arrangement the incoming call is identified to the driver via a hands-free voice interface. The driver may then accept the call, refer the call to voice mail, refer the call to a forwarding number or to terminate the call, all of which may be accomplished without the caller's knowledge. Alternatively, the call completion may be delayed shortly, with an appropriate message being provided to the caller. The system 100 may then complete the call after the short delay once it is determined that the driver's cognitive load is at an acceptable level.

The system 100 may also be adapted to take "corrective" action in the event that an on-going call is coupled with a degradation of driving performance. If after accepting a cellular telephone call the system 100 determines that the driver's cognitive load has increased beyond a threshold level and/or if there is a degradation in driving performance below a threshold level, the system 100 may automatically suspend the cellular telephone call. In such instance, a message is provided that informs the caller they are being temporarily placed on hold. The system 100 may also offer the caller an option to leave a voice mail message. Additionally, so that the driver is aware of the call interruption, an appropriate message is provided to the driver indicating that the call has been placed on hold. The driver likewise may refer the caller to voice mail.

As with other aspects of the operation of the system 100, the driver's preferences as to cellular telephone usage is provided to the system 100 via the driver identification interface 200. The system 100 may also operate with other wireless communication devices including personal digital assistants (PDAs) and pagers for receiving email and text and data messages.

To take advantage of the ability of the system 100 to prioritize incoming cellular telephone calls with other information presented to the driver requires the cellular telephone be communicatively coupled to the system 100 and controllable by the system 100. A stand-alone cellular telephone, that may not be adaptable to the system 100, may be adapted to operate in a context aware manner.

Figure 3:
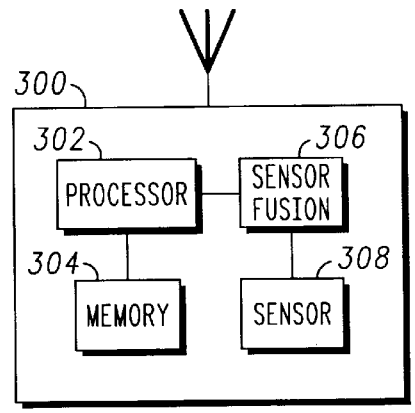
FIG. 3 is a block diagram illustration of a wireless communication device according to a preferred embodiment of the invention.

FIG. 3 illustrates a hand-held cellular telephone 300 including a processor 302, a memory 304, a sensor fusion module 306 and a plurality of sensors, one of which is illustrated as sensor 308. While shown as separate elements, it will be appreciated that these elements of the cellular telephone 300 can be integrated into a single unit or module. Alternatively, a sensor fusion module including appropriate processing capability may be provided as an add-on device to existing cellular telephones. The sensor(s) 308 may take in such data as ambient lighting, temperature, motion and speed, date and time and location. Of course, where the cellular telephone 300 is operated in a wireless communication network environment information such as location, speed, date and time may be provide by the network. However, the sensor 308 may be a GPS device capable of determining location, speed, time and day using the GPS satellite system.

The sensor fusion module 306 receives the data from the various sensors and creates a master condition list that is communicated to the processor 302 controlling the operation of the cellular telephone. The processor 302 operates in accordance with a control program stored in the memory 304 and using the master condition list to provide context aware operation of the cellular telephone 300. Context aware operation of the cellular telephone 300 can be illustrated by the following examples.

In one example of context aware operation, the cellular telephone is determined to be moving at a speed of 60 kilometers per hour (kph). This condition is reported by the sensor fusion module 306 as part of the master conditions list to the processor 302. The processor 302 infers from this speed condition that the cellular telephone is with a driver of a vehicle, and thus enters a service state where incoming calls are screened. One form of screen is as described above, wherein the caller is first advised that they are calling a driver and offered the option of leaving a voice message.

In another example of context aware operation, the cellular telephone is determined to be at approximately human body temperature. This condition is reported by the sensor fusion module 306 as part of the master conditions to the processor 302. The processor 302 operates in accordance with the control program and using the master condition list determines the cellular telephone 300 is likely located close to the user's body. Instead of operating in a ringing service state, the cellular telephone 300 is caused to operate in a vibrate service state to announce an incoming call.

The following Table I set forth various sensor mechanism, context estimates and operation service states.

TABLE I

Context Aware Wireless Device Service States

| Sensor Mechanism | Context Estimates | Service State |
|---|---|---|
| Network Infrastructure | In an airplane | No use in an airplane |
| Capability of determining location & velocity through triangulation or Doppler shift analysis Capability of recording and comparing temporally and spatially the location and velocity (above) to enable tracking Map matching database determines location relative to infrastructure, buildings, points of interest Clock/timer | In a moving vehicle Near or on a highway Not in a moving vehicle Carried by someone walking or running Time of day Day of week | (to comply with FAA regulations-subject override) Limit when driving, In intersections In cities On highways Above certain speeds Limit by location Theaters, concerts, houses of worship, etc. Limit by time of day, day of week Hours of rest, meals, meetings, family time, etc. Workday rules vs. Weekend rules Specify callers |
| Standalone Handset/ Add-on Module Location Velocity Track Light (Photometer) Temperature (Thermometer) Acceleration (vibration and orientation) (Accelerometer) Background noise (Microphone) Chemical sensor Smoke sensor Clock Altimeter | All of the above plus: How close to normal human body temperature? How likely in a purse or briefcase? (dark and sound muffled) In a pocket? (low light level, not body temperature) On a belt? Determine level of ambient noise Determine presence of chemical/smoke | If close, vibrate instead of ringing In no light and sound muffled, ring louder If in pocket but not next to body, ring instead of vibrating Vibrate instead of ringing Modulate volume of ringer and speaker relative to ambient noise level Ringing alarm |
| In-vehicle All vehicle control and accessory sensors All externally deployed sensors determining information about the driving environment All actuators and cockpit sensors to determine what the driver is doing All sensors deployed to determine the driver's condition | All of the above, plus: 1. Gaze tracker knows that driver is looking elsewhere than through the windshield or at the mirrors 2. Navigation system knows that a complicated maneuver or a dangerous curve is coming up. 3. Vehicle sensors indicates potentially dangerous degradation of the vehicle 4. Driver already engaged with a different wireless device 5. Potentially dangerous situation arises while driver already engaged | 1. If driver's glance does not return to windshield or mirrors within TBD seconds, communication diverted to voice mail. 2. Message delayed or diverted to voice mail. 3. Message delayed or diverted to voice mail. 4. Message taken 5. Call interrupted, caller offered voice mail or hold, person called informed that call is being dropped and will be resumed when safe to do so. |

TABLE I-continued

Context Aware Wireless Device Service States

| Sensor Mechanism | Context Estimates | Service State |
|---|---|---|
| | in wireless communication | |

In accordance with the preferred embodiments of the invention, methods of: assessing vehicle operator performance, informing the vehicle operator to improve the operator's performance, response synthesis in a driver assistant system, improving driver performance through performance feedback and context aware device operation are described in connection with FIGS. 4–8.

Figure 4:
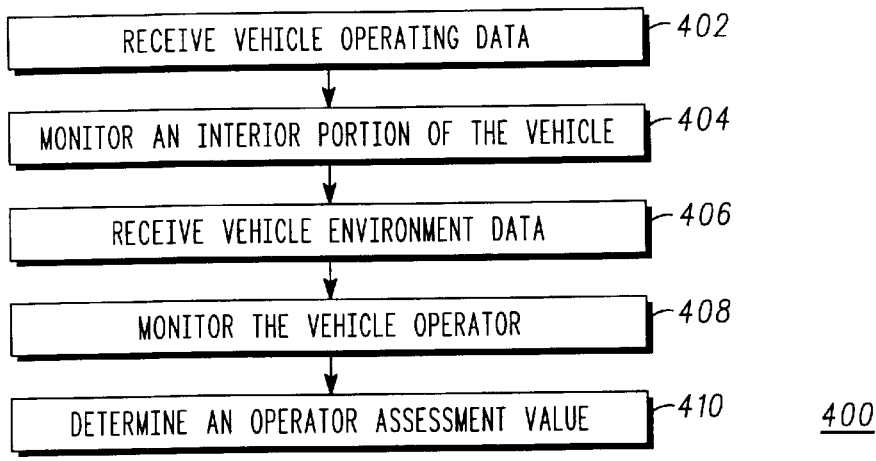
FIG. 4 is a flow chart illustrating the steps of a method of assessing vehicle operator performance in accordance with a preferred embodiment of the invention.

Referring to FIG. 4, a method 400 of assessing vehicle operator performance begins at step 402 with receiving vehicle operating data from the vehicle relating to the vehicle operating condition. Step 402 involves receiving at the sensor fusion module 102 data from the various sensors, systems and device in the vehicle data relating operation of the vehicle. This data may include vehicle speed and vehicle acceleration, throttle application, brake application, steering wheel input, throttle position, rate of change of throttle position, additional available throttle input and throttle applicator pressure, brake position, rate of change of brake position, additional available brake input and brake applicator pressure, steering wheel position, rate of change of the steering wheel, operator pressure applied to the steering wheel, additional available steering input and other operating parameter of the vehicle such as oil temp, oil pressure, coolant temp, tire pressure, brake fluid temp, brake fluid pressure, transmission temp., misfire, windshield wiper activation, front/rear defogger application, diagnostic systems, etc.

At step 404, an interior portion of the vehicle is monitored to provide data to the sensor fusion module 102 relating to activities of the driver. Monitored activities may include monitoring the usage of vehicle system controls by the driver, such as driving controls, telematics systems, infotainment systems, occupant comfort controls including HVAC, seat position, steering wheel position, pedal position, window position, sun visors, sun/moon roof and window shades and communication controls. Monitoring activities may also include monitoring activities of the vehicle passengers.

At step 406, the vehicle environment external to the vehicle is monitored to provide data to the sensor fusion module 102 relating to the operating environment of the vehicle. The operating environment data may include road condition, lane following, headway data, traffic control data and traffic condition data.

At step 408, the vehicle operator is monitored to provided data to the fusion module 102 relating to the condition of the driver. The driver physical condition may include fatigue or intoxication or a psychological condition of the driver. Additionally, a distraction level of the driver may be monitored.

At step 410 the driver performance is assessed. The driver's performance may be assessed by inferring driver performance from the vehicle operating data, the operator activity data, the environment data and the operator condition data. Such an inference may be drawn using inference engine or a rules-based decision engine. Alternatively, fuzzy logic or adaptive, goal-seeking may be used.

Figure 5:
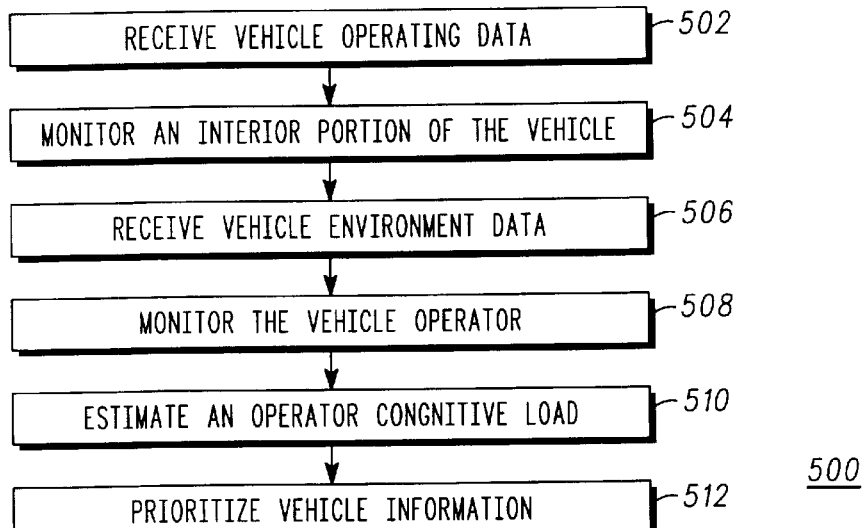
FIG. 5 is a flow chart illustrating the steps of a method of improving vehicle operator performance in accordance with a preferred embodiment of the invention.

Referring to FIG. 5, a method 500 of informing a driver to improve driver performance begins at step 502 with receiving vehicle operating data from the vehicle relating to the vehicle operating condition. Step 502 involves receiving at the sensor fusion module 102 data from the various sensors, systems and device in the vehicle data relating operation of the vehicle. This data may include vehicle speed and vehicle acceleration, throttle application, brake application, steering wheel input, throttle position, rate of change of throttle position, additional available throttle input and throttle applicator pressure, brake position, rate of change of brake position, additional available brake input and brake applicator pressure, steering wheel position, rate of change of the steering wheel, operator pressure applied to the steering wheel, additional available steering input and other operating parameter of the vehicle such as oil temp, oil pressure, coolant temp, tire pressure, brake fluid temp, brake fluid pressure, transmission temp., misfire, windshield wiper activation, front/rear defogger application, diagnostic systems, etc.

At step 504, an interior portion of the vehicle is monitored to provide data to the sensor fusion module 102 relating to activities of the driver. Monitored activities may include monitoring the usage of vehicle system controls by the driver, such as driving controls, telematics systems, infotainment systems, occupant comfort controls including HVAC, seat position, steering wheel position, pedal position, window position, sun visors, sun/moon roof and window shades and communication controls. Monitoring activities may also include monitoring activities of the vehicle passengers.

At step 506, the vehicle environment external to the vehicle is monitored to provide data to the sensor fusion module 102 relating to the operating environment of the vehicle. The operating environment data may include road condition, lane following, headway data, traffic control data and traffic condition data.

At step 508, the vehicle operator is monitored to provided data to the fusion module 102 relating to the condition of the driver. The driver physical condition may include fatigue or intoxication or a psychological condition of the driver. Additionally, a distraction level of the driver may be monitored.

At step 510, the driver's cognitive load is estimated. The driver's cognitive load may take into account driver preferences, past performance and habits. Then, at step 512, vehicle information is prioritized based upon the driver's cognitive load for communication to the driver.

Figure 6:
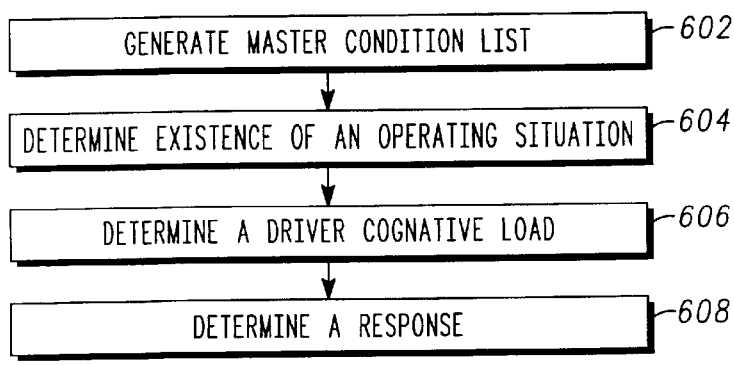
FIG. 6 is a flow chart illustrating the steps of a method of synthesizing a response to vehicle operating conditions in accordance with a preferred embodiment of the invention.

Referring to FIG. 6, a method 600 of synthesizing a response to an operating situation of a vehicle begins at step 602 with the generation of a master condition list. The master condition list is generated by the sensor fusion module 102 and is a fusion of the various sensor data available within the vehicle. The sensor data may be any available data within the vehicle including: vehicle operating data, driver activity data, environment data, driver condition data, driver preference data, driver action feedback data.

From the master condition list, at step 604, an operating situation is determined. The operating condition may be: the existence of a problem condition, the existence of a problem correction, the existence of a problem escalation, the existence of an operator task requirement, the existence of an agent task requirement, the existence of a completion of an operator task, the existence of a completion of an agent task. Additionally, at step 606, an operator cognitive load is determined.

At step 608, a response to the operating situation is determined based on the operator cognitive load. The response may be synchronizing an information flow to the driver, generating an alert to the driver, providing an alert including audio alerts, a visual alerts and haptic alerts, suspending or terminating operation of selected services within the vehicle.

Figure 7:
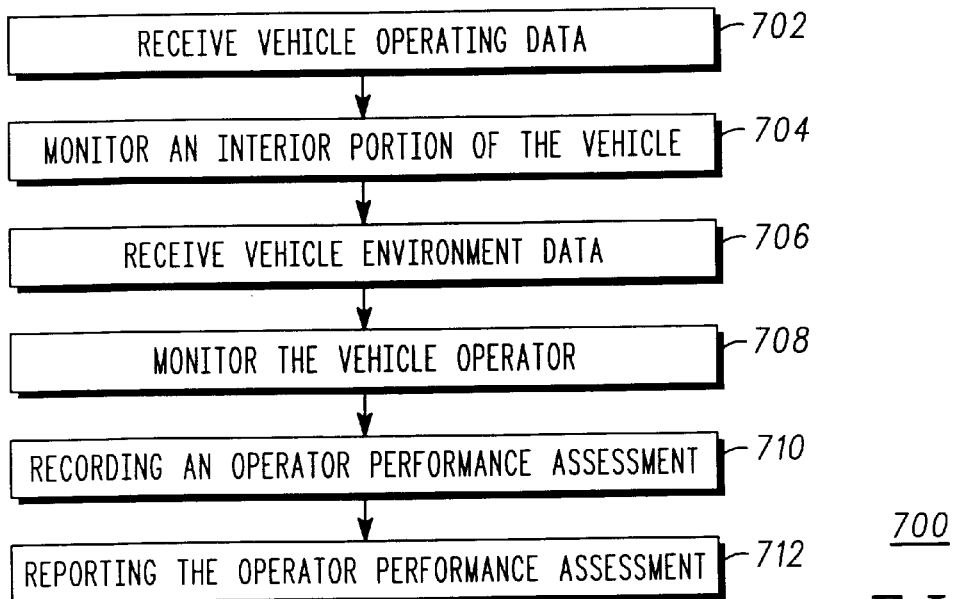
FIG. 7 is a flow chart illustrating the steps of a method of providing feedback to a vehicle operator in accordance with a preferred embodiment of the invention.

Referring to FIG. 7, a method 700 of improving driver performance through performance feedback begins at step 702 with receiving vehicle operating data from the vehicle relating to the vehicle operating condition. Step 702 involves receiving at the sensor fusion module 102 data from the various sensors, systems and devices in the vehicle and data relating operation of the vehicle. This data may include vehicle speed and vehicle acceleration, throttle application, brake application, steering wheel input, throttle position, rate of change of throttle position, additional available throttle input and throttle applicator pressure, brake position, rate of change of brake position, additional available brake input and brake applicator pressure, steering wheel position, rate of change of the steering wheel, operator pressure applied to the steering wheel, additional available steering input and other operating parameter of the vehicle such as oil temp, oil pressure, coolant temp, tire pressure, brake fluid temp, brake fluid pressure, transmission temp., misfire, windshield wiper activation, front/rear defogger application, diagnostic systems, etc.

At step 704, an interior portion of the vehicle is monitored to provide data to the sensor fusion module 102 relating to activities of the driver. Monitored activities may include monitoring the usage of vehicle system controls by the driver, such as driving controls, telematics systems, infotainment systems, occupant comfort controls including HVAC, seat position, steering wheel position, pedal position, window position, sun visors, sun/moon roof and window shades and communication controls. Monitoring activities may also include monitoring activities of the vehicle passengers.

At step 706, the vehicle environment external to the vehicle is monitored to provide data to the sensor fusion module 102 relating to the operating environment of the vehicle. The operating environment data may include road condition, lane following, headway data, traffic control data and traffic condition data.

At step 708, the vehicle operator is monitored to provided data to the fusion module 102 relating to the condition of the driver. The driver's physical condition may include fatigue or intoxication or a psychological condition of the driver. Additionally, a distraction level of the driver may be monitored.

At step 710, the driver's performance assessment is determined and is recorded so that at step 712, the driver's performance assessment may be reported to the driver. Step 712 includes reporting the driver performance assessment upon conclusion of vehicle operation or reporting the operator performance assessment during operation of the vehicle. Moreover, the driver's performance assessment may be recorded for a first period of vehicle operation and for a second period of vehicle operation and include a comparison of the two performances.

The method may further include the step of receiving driver preference data and recording the driver performance assessment based on the driver preference data. Additionally, the driver performance assessment may include a score for each of a plurality of aspects of vehicle operation. Reporting the driver performance assessment may be by visual indication, audio indication or haptic indication.

Figure 8:
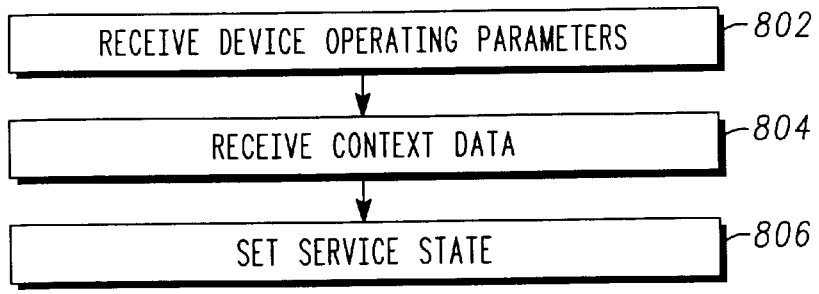
FIG. 8 is a flow chart illustrating the steps of a method of configuring a service state of a wireless communication device in accordance with a preferred embodiment of the invention.

Referring to FIG. 8, a method 800 for configuring a service state of a wireless communication device begins at step 802 with receiving a set of device operating parameters defining a preferred service state of the wireless communication device for a device operator. At step 804, context data is received from at least one context data source. The device operating parameters includes at least a context parameter. The context parameter and the context data may each relate to: a speed of the wireless communication device, a location of the wireless communication device, time, an activity of the device operator, a cognitive load of the device operator, an operation of a vehicle including vehicle operating data and environment data, ambient lighting, altitude and ambient sound. The data received may be a fusion of data from a variety of sources, such as from within the vehicle where the wireless communication device is communicatively coupled to the vehicle. The device operating parameters may be provided via a personal portable user interface, such as vehicle identification interface 200.

At step 806, a service state of the wireless communication device is set. The service state may be: call forwarding, call forwarding to voice mail, voice activated, ringing mode, call completion delay and calling party identification, etc.

The wireless communication device may be a cellular telephone, a pager, a personal digital assistant or other computing device including personal computers and web browsers.

The invention has been described in terms of several preferred embodiments, and particularly to systems and methods for synthesizing and summarizing information and the presentation of information to a driver. Modifications and alternative embodiments of the invention will be apparent to those skilled in the art in view of the foregoing description. This description is to be construed as illustrative only, and is for the purpose of teaching those skilled in the art the best mode of carrying out the invention. The details of the structure and method may be varied substantially without departing from the spirit of the invention, and the exclusive use of all modifications, which come within the scope of the appended claims is reserved.

We claim:

1. A method for managing the response of a driver-vehicle information system; said method comprising:
generating a condition list, the condition list being a discrete set of parameters formed from gathered sensor data;
determining the existence of an operating situation;
determining a driver cognitive load based upon the operating situation, the cognitive load being a measure of work needed to manage a particular task; and
determining a response to the operating situation.

2. The method of claim 1, wherein the driver-vehicle information system comprises a system capable of providing the operator of a vehicle with information regarding one of vehicle operation, vehicle environment, and vehicle driver.

3. The method of claim 1, wherein the step of generating a condition list comprises translating sensor data into discrete states that describe the condition being measured.

4. The method of claim 1, wherein the step of determining the existence of an operating situation comprises interpreting the condition list to determine a state of operation of the vehicle.

5. The method of claim 1, wherein the state of operation comprises a state of operation selected from the group of states of operation comprising:
condition of vehicle systems;

condition of vehicle internal environment;

condition of vehicle external environment;

driver condition; and driver preferences.

6. The method of claim 1, wherein the step of determining the existence of an operating situation comprises interpreting the condition list to determine the existence of a problem.

7. The method of claim 1, wherein the step of determining the existence of an operating situation comprises interpreting the condition list to determine the existence of a problem correction.

8. The method of claim 1, wherein the step of determining the existence of an operating situation comprises interpreting the condition list to determine the existence of a problem exacerbation.

9. The method of claim 1, wherein the work needed to manage a task comprises of at least one of mental work and physical work.

10. The method of claim 1, wherein the step of determining a response to the operating situation comprises determining a priority of problems of an operating situation in view of one of driver cognitive load and operating situation.

11. The method of claim 1, wherein the step of determining a response to the operating situation comprises determining the urgency of notification of the operating situation in view of the driver cognitive load.

12. The method of claim 1, wherein the step of determining a response to the operating situation comprises ordering information flow regarding the operating situation to the driver of the vehicle based on the safety of the driver.

13. The method of claim 1, wherein the step of determining a response to the operating situation comprises a response from the group of responses comprising:

generating an alert to the driver;

initiating operation of selected services within the vehicle; and terminating operation of selected services within the vehicle.

14. The method of claim 1 further comprises the step of providing feedback to the operator.

15. The method of claim 1, wherein the feedback comprises feedback from the group of feedback comprising:

driver performance information, and driver training information.

16. A method for managing the response of a communication device; said method comprising of:

generating a condition list, the condition list being a discrete set of parameters formed from gathered sensor data;

determining the existence of an operating situation wherein the step of determining the existence of an operating situation comprises interpreting the condition list to determine at least one of the state of the operator of the device and the state of the device; and determining a response to the operating situation.

17. The method of claim 15, wherein the communication device comprises a system providing two-way communication with the operator of the device.

18. The method of claim 15, wherein the sensor data comprises sensor data from the group of sensor data comprising:

location of operator;

altitude of operator;

velocity of operator;

acceleration of operator;

background noise near operator; and chemical composition of environment surrounding operator.

19. The method of claim 15, wherein the step of generating a condition list comprises translating sensor data into discrete states that describe the condition being measured.

20. The method of claim 15, wherein the step of determining a response to the operating situation comprises a response from the group of responses comprising:

generating an alert to the operator of the device;

initiating operation of selected services of the communication device; and terminating operation of selected services of the communication device.

* * * * *